United States Patent [19]

Mächler et al.

[11] Patent Number: 4,660,974
[45] Date of Patent: Apr. 28, 1987

[54] ARRANGEMENT FOR DETERMINING THE SPECTRAL CHARACTERISTIC OF THE REFRACTIVE INDEX OF A FLUID

[75] Inventors: Meinrad Mächler, Ellwangen; Richard Sachse, Königsbronn; Harry Schlemmer, Aalen, all of Fed. Rep. of Germany

[73] Assignee: Carl-Zeiss-Stiftung, Heidenheim, Fed. Rep. of Germany

[21] Appl. No.: 722,111

[22] Filed: Apr. 11, 1985

[30] Foreign Application Priority Data

Apr. 14, 1984 [DE] Fed. Rep. of Germany ....... 3414261

[51] Int. Cl.⁴ ............................................. G01N 21/41
[52] U.S. Cl. .................................... 356/128; 356/328
[58] Field of Search ............... 356/128, 317, 318, 326, 356/328, 357, 361

[56] References Cited

U.S. PATENT DOCUMENTS 4,377,343 3/1983 Monson ............................... 356/357

Primary Examiner—Eugene R. LaRoche
Assistant Examiner—James C. Lee
Attorney, Agent, or Firm—Walter Ottesen

[57] ABSTRACT

The invention is directed to an arrangement for determining the spectral characteristic of the refractive index of a liquid or a gas wherein the specimen is enclosed between two boundary surfaces spaced apart between 1 and 50 μm. The surfaces are at least approximately parallel to each other. The boundary surfaces cause interferences when illuminated with white light passing through the surfaces. The interferences are measured by a spectrometer in their wavelength-dependent course and are thereafter evaluated.

17 Claims, 4 Drawing Figures

ARRANGEMENT FOR DETERMINING THE SPECTRAL CHARACTERISTIC OF THE REFRACTIVE INDEX OF A FLUID

FIELD OF THE INVENTION

The invention relates to an arrangement for determining the spectral characteristic of the refractive index (dispersion) of a fluid with a device for illuminating the fluid with a white light for generating interferences. The invention relates especially to the measurement of very small volumes as they occur, for example, in the area of high-pressure fluid chromatography and especially with respect to micro high-pressure fluid chromatography.

BACKGROUND OF THE INVENTION

The measurement of refractive indices of fluids with the aid of two-beam interferometers has been known for some time. The two-beam interferometers base the measurement of the refractive index on a comparison of the optical wavelengths in two cells separated from one another and which are geometrically identical. The substance to be investigated is in one cell and another substance with a known refractive index is in the other cell. In lieu of another substance, a vacuum can be established in the other cell.

In most interferometers of this kind, two fringe systems are generated by means of two separate but like beam paths of which the one beam path does not pass through the object to be measured and therefore remains unchanged during the measurement and thus serves as a readout index for the other fringe system which becomes changed by the measurement. Interferometers with two fringe systems afford the advantage that they are substantially insensitive to influences of temperature and mechanical deformation of the apparatus.

The refractive index is determined in that the excursion of the fringe system is either read off a scale or in that the fringes are shifted again into the zero position by means of an optical compensator in the beam path of the measuring cell whereby the magnitude of the displacement provides the measured value. Interferometers of this type are described, for example, in German Pat. No. 10 22 032 or in German published patent application DE-OS 25 07 183.

German Pat. No. 23 06 091 describes an interference refractometer wherein the measurement and reference cells are configured as separate Fabry-Perot interferometers having lengths which are periodically changed with the aid of a common electro-strictive apparatus. Both cells have curved interference mirrors of spherical shape with a high reflectivity so that the light radiated into the mirror exits only after a great many reflections. When passing through the region of the electro-strictive apparatus, sharply limited resonance transmittances occur with monochromatic light which are sharply defined with respect to comparatively wide ranges in which the cells are opaque. If a medium having a changed index of refraction gets into the measuring cell, the resonance frequencies of the measuring cell become displaced with respect to the resonance frequencies of the reference cell via the change of the optical path length. The magnitude of the displacement is a measure of the change of the index of refraction. Disturbing influences which change the resonance frequencies of both cells in the same manner do not affect the measurement.

With the above-described apparatus, the determination of the refractive index in dependence upon wavelength is only possible, if at all, by making individual measurements at various wavelengths which is complex and takes an inordinate amount of time.

German Pat. No. 21 53 315 discloses an interference spectral photometer wherein the spectral characteristic of the refractive index or the transmittance of a specimen is determined. In this arrangement, the light beam emanating from a continuous radiator is divided into two component light beams which are intensity modulated at different frequencies. The two component beams pass through an interferometer arrangement parallel to one another and each component beam is split up into two subcomponent beams and again united and conducted to a common beam receiver. The interferometer arrangement includes a scanning mirror for adjusting changes of the optical path differences of one interferometer branch. From an evaluation of the receiver signal, the interferometer arrangement simultaneously delivers the specimen interferogram and the background interferogram because of the two component beams. The spectral characteristic of the refractive index or the transmittance of the specimen is obtained with the aid of a suitable computer from the specimen and background interferograms.

Practical applications of this arrangement for measuring the refractive index are not known and this is not surprising because the dispersion in the spectral range of 5 to 500 $\mu$m specified for the arrangement is not especially interesting. Furthermore, the arrangement is also not suitable for measurements where intense absorption is present.

Finally, it is known from the literature that the refractive index can be determined from the interference superpositions with transmission spectrums or reflection spectrums. In spectroscopy with known indices of refraction, the precise layer thickness is determined mostly from the interference superpositions. However, work also is known wherein with the layer thickness known, the refractive index is determined. Thus, for example, an article entitled "The Index of Refraction of Germanium Measured by an Interference Method" by D. H. Rank et al in the Journal of the Optical Society of America, Volume 44, Number 1, (January, 1954), pages 13 to 16, describes that the refractive index of a germanium crystal having a thickness of 3 mm is determined in the wavelength range of 2.0 to 2.4 $\mu$m by evaluating the interference superpositions of the transmission spectrum. An article entitled "Determination of Refractive Index and Film Thickness from Interference Fringes" by N. J. Harrik in Applied Optics, Volume 10, Number 10, (October 1971), pages 2344 to 2349, discloses that the refractive index in the range of 2.5 to 7.0 $\mu$m as well as the thickness of films are determined by measuring the reflective spectrum at various angles of incidence.

The known arrangements are not suitable for making measurements on very small volumes of fluid as is the situation, for example, with high-pressure fluid chromatography and especially with micro high-pressure fluid chromatography. In this area, there is also the requirement to be able to measure into the ultraviolet range. The known arrangements are further poorly suited or not at all suitable where intense absorption is present and for specimens for which the danger of a thermal or photochemical decomposition is present because of the radiation energy for making measurements which is directed to the specimen.

SUMMARY OF THE INVENTION

In view of the foregoing, it is an object of the invention to provide an arrangement for measuring the spectral characteristic of the refractive index into the ultraviolet range for fluids so as to include also very small specimen volumes of fluids (gases or liquids). It is a further object of the invention to provide such an arrangement wherein such measurements are made in the presence of intense absorption while at the same time permitting the measurement to be conducted in a simple manner suitable for a routine assignment. It is a still further object of the invention to provide such an arrangement wherein the radiation to which the specimen is subjected is held as low as possible for substances for which there is the danger of a change in the specimen from the radiation used for measurement because of the very small volume thereof. Another object of the invention is to provide an arrangement wherein continuous measurements are possible and changes in the range of 0.01 second are still detected.

The arrangement of the invention is for determining the spectral characteristic of the refractive index of a fluid which can be a gas or a liquid and includes an illuminating device for illuminating the fluid with white light for generating interferences. The arrangement further includes a light-transmitting window mounted at a fixed spacing of between 1 and 50 μm in front of a second light-transmitting window or in front of a boundary part which is preferably at least partially reflective. The surfaces defining the fixed spacing are at least approximately parallel to each other and constitute boundary surfaces to the fluid which generate component light bundles. A measuring device measures the wavelength-dependent intensity characteristic of the interfering component light bundles.

In an advantageous embodiment of the invention, a diode-array spectrometer is provided for the measurement of the wavelength dependent intensity characteristic and which is connected via an electronic unit with an evaluation computer.

In one embodiment of the invention, two light-transmitting windows are arranged as parts of a through-flow cuvette to provide a continuous determination of the spectral characteristic of the index of refraction. In another embodiment, the light-transmitting window and the above-mentioned boundary part are arranged as parts of a through-flow cuvette to provide the continuous determination of the spectral characteristic of the index of refraction.

It is especially advantageous to provide light conductors for the conduction of the white light to the fluid for illumination and for the measurement since in this way, the measuring location is separated from the rest of the measuring arrangement and the through-flow cuvette is mounted directly behind the separation column, for example, as in the case of fluid chromatography.

In a further advantageous embodiment of the invention, the light reflected in the direction of the incoming light is provided for making the measurement. For this purpose, the second surface bounding the liquid or the gas is not configured as a window; instead, it is configured as a reflecting boundary part. It is useful to make this component out of a good heat conducting material and, in the event that its heat capacity is insufficient for small specimen volumes to conduct heat away, the component should be connected with a temperature regulating device.

For a further reduction of the radiation load on the specimen, a filter or a double monochromator with oppositely directed dispersion can be mounted between the specimen and the illuminating device.

An advantage of the arrangement according to the invention is especially to be seen for high-pressure fluid chromatography in that, depending upon the requirements and the specimen material, measurements can be made either in the range of absorption for the purpose of increased sensitivity and of information content or, measurements can be made next to the absorption bands in connection with radiation sensitive specimens. Generally, a measurement within the absorption bands is necessary for identifying individual substances. In contrast, a measurement of the index of refraction outside of the absorption bands is sufficient for the quantitative determination of individual known substances.

In contrast to the foregoing, one is dependent upon the measurement in a range of intense absorption when making absorption measurements also for quantitative determinations when dealing with high-pressure fluid chromatography as a consequence of the low specimen volumes in order to obtain an adequate sensitivity. Since absorption measurements are perforce connected with energy absorption, a measurement of this type of radiation sensitive specimens is always associated with disadvantages.

The advantage of the refraction index measurements is that they are useful for quantitative measurements in wavelength ranges with no or little absorption and also for radiation sensitive specimens. A further advantage of such measurements is that they provide a substantial increase of the sensitivity and of the measuring precision in wavelength ranges with intense absorption in connection with small specimen volumes as compared to absorption measurements or through a lower intensity of the radiation used for measurement, a lower thermal loading of the specimen is made possible. The measurement of the index of refraction characteristic in one wavelength range provides an increase in the sensitivity and measuring precision in both cases as compared to the measurement in only one wavelength.

BRIEF DESCRIPTION OF THE DRAWING

The invention will now be described with reference to the drawing wherein.

DESCRIPTION OF THE PREFERRED EMBODIMENTS OF THE INVENTION

Figure 1:
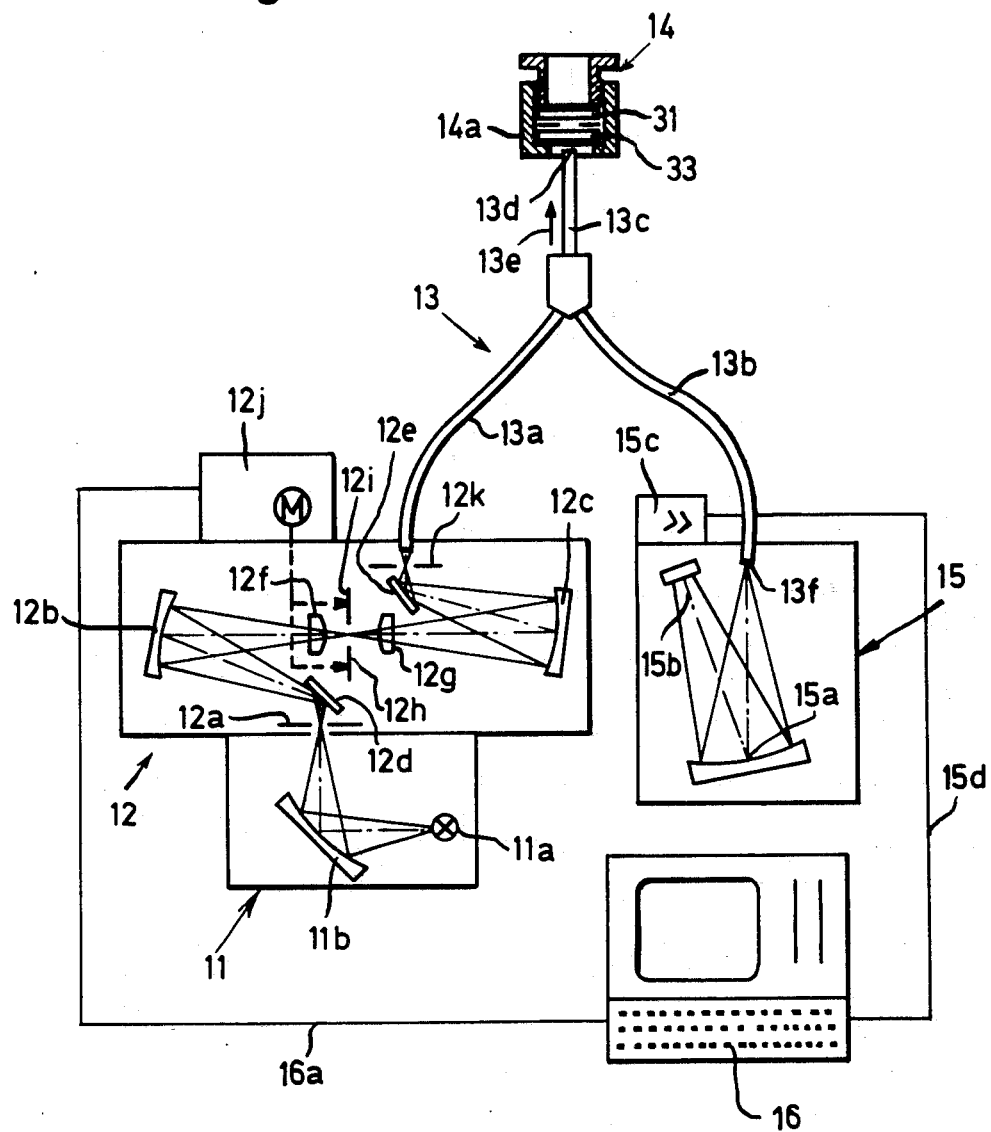
FIG. 1 is a schematic representation of the entire arrangement according to the invention.

In FIG. 1, reference numeral 11 identifies the illuminating device which comprises a light source 11a, for example a xenon lamp generating white light, and an elliptical concave mirror 11b. The concave mirror 11b images the light source 11a at the entrance slit 12a of a double monochromator 12 with oppositely directed dispersion. The double monochromator is described in German published patent application No. DE-OS 29 19 925 and comprises two like monochromators with concave gratings 12b and 12c, two deflecting mirrors 12d and 12e, two field lenses 12f and 12g and the exit slit 12k. The concave grating 12b generates a spectrum of the light source 11a in the plane of the slit jaws 12h and 12i of the central slit. The slit jaws 12h and 12i mask out the desired range from this spectrum. The slit jaws 12h and 12i are adjustable independently of each other by means of a device 12j which contains two step motors. The spectral range which is passed by the slit jaws 12h and 12i is imaged on the exit slit 12k by the concave grating 12c. All wavelengths which are passed through are superposed because of the like configuration of the two monochromators so that a continuum of a limited wavelength range is produced at the exit slit 12k.

The branch 13a of a branched light conductor 13 is arranged behind the exit slit 12k of the double monochromator 12. The branch 13a collects the rays of the illuminating device which have been passed through by the double monochromator 12 and conducts the same to the cuvette 14. The light conductor branches 13a and 13b are assembled from a plurality of light conducting fibers which are arranged in common one next to the other in branch 13c. The light conducting fibers of branch 13b collect the light reflected from the cuvette and conduct the same to the spectrometer 15. The common end 13d of all light conducting fibers is spaced a short distance from the cuvette window 33 and the most favorable value of this spacing is easily determined empirically. The arrangement of the light conducting fibers which, on the one hand, belong to branch 13a and, on the other hand, which belong to branch 13b can be statistic to each other at the common end 13d.

The light conducting fibers are arranged in the form of a slit at the end 13f of the light conducting branch 13b so that their end surfaces replace the entrance slit which is otherwise present in spectrometers. For this reason, the spectrometer comprises only a concave grating 15a and the diode array 15b which is connected to an electronic unit 15c. The signals of the diode array 15b are preprocessed by the electronic unit 15c and transmitted to a computer 16 via a conductor 15d. The evaluation is performed in the computer 16d and will be explained in greater detail below.

The computer 16 is also connected with the electronic unit 12j via conductor 16a. The electronic unit 12j controls the two step motors which move the slit jaws 12h and 12i of the central slit of the double monochromator 12. In this way, the central slit can be adjusted either pursuant to a predetermined program; or, the slit can be controlled by the values of the refractive index ascertained by the computer and from which the wavelength ranges having an intense absorption can be determined. With this last-mentioned control, the slit is controlled by the computer in such a manner that the thermal load to which the specimen is subjected remains small. Since a measurement of the entire refractive index characteristic takes less than 0.01 second, the radiation for most specimens can be maintained sufficiently low during this time. The computer always evaluates only the measurements in the particular wavelength ranges in which the specimen is subjected to radiation.

It is advantageous to configure the spectrometer so that it has an aperture ratio which accepts the aperture of the light conducting branch 13b without any trimming. This is possible with concave gratings that are holographically recorded as disclosed in German published patent application No. DE-OS 32 15 879.

It is understood that the branched light conductor 13 can be configured at its three ends so as to be equipped with easy to use pin and socket connectors to connect the conductor 13 to the double monochromator 12, the cuvette 14 and the spectrometer 15 whereby a precisely defined positioning of the light-conducting fiber ends is possible. Connecting parts of this kind are also disclosed in DE-OS No. 32 15 879.

Figure 2:
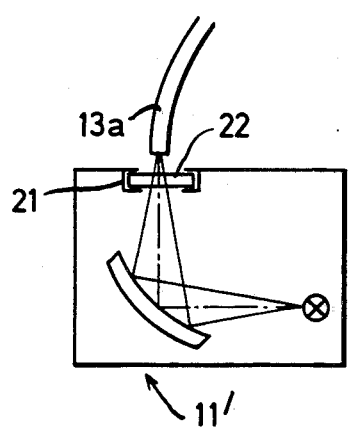
FIG. 2 is a schematic of a simplified embodiment of the illuminating device.

A simpler embodiment for the illuminating device is shown in FIG. 2 wherein the latter is identified by reference numeral 11'. In this embodiment, the light-conducting branch 13a is connected directly to the illuminating device 11'. A filter compartment 21 is provided in the illuminating device 11' and serves as a substitute for the double monochromator 12 utilized in the embodiment of FIG. 1. Different filters 22 can be inserted into the filter compartment 21 having transmission characteristics which are determined to accommodate the specimens to be measured and their radiation sensitive wavelength ranges. It is understood that filters can be omitted for specimens which are not sensitive to radiation.

Figure 3:
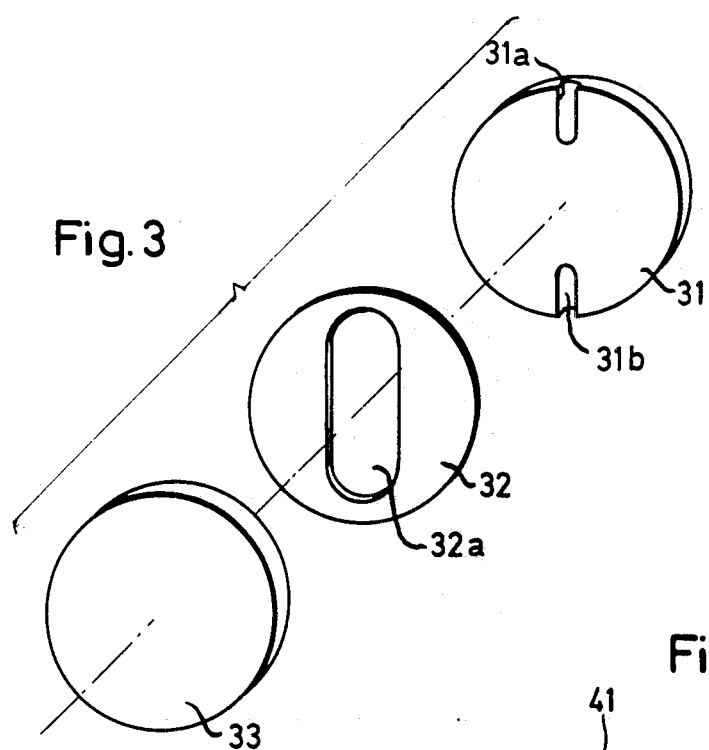
FIG. 3 is a schematic representation of a suitable through-flow cuvette.

FIG. 3 shows details of one embodiment of the cuvette identified in FIG. 1 by reference numeral 14. The receptacle identified in FIG. 1 by reference numeral 14a is not drawn to scale. The two windows 31 and 33 made of optically transmitting material and the spacer foil 32 are seated in the receptacle 14a. An inlet channel 31a and an outlet channel 31b are milled into the window 31. The spacer foil 32 has a cutout 32a for the measuring chamber and for the inner ends of the channels 31a and 31b. A through-flow cuvette with the layer thickness of the spacer foil 32 is provided when all three parts 31, 32 and 33 are pressed one atop the other, for example, in the threaded receptacle 14a of FIG. 1. A cuvette of this type can also be used for making a one time measurement by filling and emptying the cuvette with a suitable piston injector having a point adapted to fit into the channel 31b.

For high-pressure fluid chromatography, the capillaries of the column are inserted into the channels 31a and 31b. Suitable cylindrically-shaped seals made of elastic material surround the capillaries at the outer ends of the channels 31a and 31b and are pressed together in the direction of the capillary axes. By means of these seals, a cuvette of this type can also be used as a pressure-tight through-flow cuvette.

Figure 4:
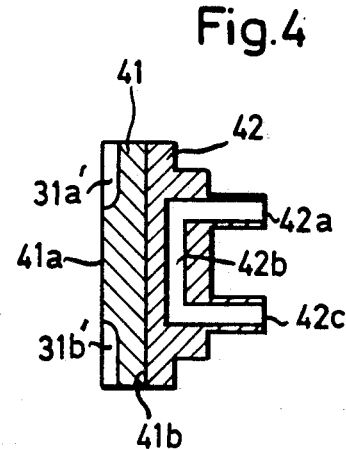
FIG. 4 is an elevation view, in section, of a reflecting boundary part for the through-flow cuvette.

If light reflected in the beam direction 13e is utilized for making the measurement as shown in FIG. 1, the light transmitting window 31 in FIG. 3 can be replaced by the assembly shown in FIG. 4. In this embodiment, reference numeral 41 identifies a boundary part having the same dimensions as the light transmitting window 31. Also the inlet channel 31a' and the outlet channel 31b are configured in the same manner. However, the boundary part 41 is made of a material having a good thermal conductivity. Its surface 41a should have approximately the same reflectivity as the material of the window 33. The boundary part 41 does not have to be made of light transmitting material; however, it must be capable of being polished. A suitable material is, for example, beryllium oxide or aluminum nitrate which is a compacted ceramic to which a mirror layer made of platinum, iridium or rhodium can be vaporized or galvanically applied. The rear surface 41b of the boundary part 41a is likewise planar so that a good heat contact to the temperature regulating part 42 is provided. The temperature regulating part 42 has tube connectors 42a and 42c as well as a temperature channel 42b and is connected to a liquid thermostat (not shown). It is understood that a Peltier element can be used in lieu of the temperature regulating part 42.

Decisive in this assembly is that there be a good heat contact to the relatively thin fluid layer on the surface 41a by means of which a good temperature regulation of the specimen is obtained and which for many substances is then sufficient when the light conducted thereto for the measurement is absorbed. For a portion of the applications, the heat capacity of the boundary part 41 is sufficient because of the small volume of the specimen so that a temperature regulating arrangement is not required.

For the layer thickness range of 1 to 50 μm, cuvettes which can be disassembled are preferably used because only with these units is a trouble-free cleaning possible. Therefore, for a precise measurement, the exact layer thickness of the assembled cuvette must first be determined. This determination can be made either on the cuvette filled with air or another gas or on the cuvette which is filled with liquid and under pressure which is, above all, better in connection with the high-pressure fluid chromatography because of the influence of the pressure. This determination is made at the beginning of a high-pressure fluid chromatographic measurement with a pure solution.

Assuming that the index of refraction characteristic (dispersion) is known for the gas or the liquid utilized, the exact layer thickness can be computed with the following equation:

$$d = \frac{\lambda_a \lambda_e P}{2|n(\lambda_e)\lambda_a - n(\lambda_a)\lambda_e|}$$

In the above, $\lambda_a$ and $\lambda_e$ are wavelengths in which maxima and minima occur as a consequence of interference in the measured intensity and P is the number of periods between the extremes (P = 1 for the spacing of one maximum to the next maximum). A high precision is obtained if the number of periods is large and it is therefore useful to measure in a wavelength range (and/or at a specimen) wherein the index of refraction varies little or not at all. (Phase jumps on the boundary surfaces have practically no influence since they are constant in the wavelength ranges which are in question.)

After the exact layer thickness of the cuvette is determined in this manner, the index of refraction characteristic n(λ) from the specimens in the cuvette can be determined on the basis of the maxima or minima occurring as a consequence of interference from the following equation:

$$n_{ij} = \frac{\lambda_i \lambda_j P}{2d|\lambda_i - \lambda_j|}$$

wherein $n_{ij}$ is the mean index of refraction for the wavelength interval from $\lambda_i$ to $\lambda_j$ whereby $\lambda_i$ and $\lambda_j$ are both wavelengths wherein a maximum or minimum is present; P is again the number of periods between these extremes.

In order to obtain the most precise values with changes of the index of refraction, the intervals $\lambda_i$ to $\lambda_j$ are selected to be as small as possible. In this way, a large relative error dn/n ≈dλ/λ₁−λⱼis obtained. However, this error can be avoided by the procedure delineated below if the specimen to be measured does not exhibit a change in the index of refraction which is too great in a wavelength range. In this procedure, maximum is present for $\lambda_j$, then the following is applicable for the ordinal number:

$$m_j \approx \frac{2n_{ij}d}{\lambda_j}$$

In this connection, one makes it a condition precedent that $n_{ij} \approx n_j$. The error which then occurs leads to a numerical value for $m_j$ which is not a whole number and which can be eliminated by rounding off to the next whole value. Thereafter, the index of refraction for all extreme values can be obtained by means of a simple counting off pursuant to the equation:

$$n = m\frac{\lambda}{2d}$$

The relative errors that then occur amount to only dn/n =dλ/λ.

It is understood that the foregoing description is that of the preferred embodiments of the invention and that various changes and modifications may be made thereto without departing from the spirit and scope of the invention as defined in the appended claims.

What is claimed is:

1. An arrangement for determining the spectral characteristic of the refractive index of a fluid comprising:
   a boundary part having a first surface which is at least partially reflective;
   a light transmitting window having a second surface substantially parallel to said first surface and being mounted at a spacing of 1 to 50 μm in front of said boundary part for accommodating the fluid therebetween;
   illuminating means for illuminating the fluid with white light;
   said first and second surfaces defining respective boundary surfaces to said fluid for causing a plurality of interfering component beams of light; and,
   measuring means for measuring the wavelength-dependent intensity characteristic of said interfering componsent beams of light.

2. The arrangement of claim 1, said measuring means being a diode-array spectrometer for providing output signals and said arrangement further comprising: an electronic unit for preprocessing the output signals of said spectrometer; and, an evaluation computer connected to said electronic unit.

3. The arrangement of claim 1, said illuminating means comprising: light conducting means for conducting light into said fluid in a predetermined direction, said first surface of said boundary part reflecting said light in said predetermined direction; and, further light conducting means for conducting said reflected light to said measuring means.

4. The arrangement of claim 3, comprising temperature regulating means for regulating the temperature of said boundary part.

5. The arrangement of claim 3, said first-mentioned light conducting means and said further light conducting means both consisting of light conductors.

6. The arrangement of claim 3, said illuminating means comprising an illuminating device for generating said white light; said first-mentioned light conducting means and said further light conducting means being a branched light conductor having a first branch communicating with said illuminating device and a second branch communicating with said measuring means, said branched light conductor having a common branch end mounted in front of said light transmitting window.

7. The arrangement of claim 6, wherein the fluid is intensely absorbent in a predetermined wavelength range, the arrangement further comprising filter means disposed between said illuminating device and said light transmitting window, said filter means being dimensioned so as to have a low transmittance in said predetermined wavelength range so that said measuring means delivers no measured value output in said predetermined wavelength range.

8. The arrangement of claim 6, wherein the fluid is partially absorbent in a predetermined wavelength range, and the arrangement further comprising a double monochromator having oppositely directed dispersion, said double monochromator being disposed between said illuminating device and said light transmitting window and including adjustable central slit means for passing only said predetermined wavelength range so that said measuring means delivers a measured value output in said predetermined wavelength range.

9. The arrangement of claim 8, said double monochromator including electric control means for adjusting said central slit means, said electric control means being connected to said computer.

10. An arrangement for determining the spectral characteristic of the refractive index of a fluid comprising:
  a cuvette for accommodating the fluid, said cuvette including:
    a first light transmitting window having a first surface;
    a second light transmitting window mounted adjacent said first light transmitting window and having a second surface substantially parallel to said first surface; and,
    spacing means for spacing said first surface from said second surface a distance of 1 to 50 μm to define a chamber between said first and second surfaces for accommodating the fluid therein;
  illuminating means for illuminating the fluid with white light;
  said first and second surfaces defining respective boundary surfaces to said fluid for causing a plurality of interfering component beams of light; and,
  measuring means for measuring the wavelength-dependent intensity characteristic of said interfering component beams of light.

11. The arrangement of claim 10, said measuring means being a diode-array spectrometer for providing output signals and said arrangement further comprising: an electronic unit for preprocessing the output signals of said spectrometer; and, an evaluation computer connected to said electronic unit.

12. The arrangement of claim 10, said illuminating means comprising: light conducting means for conducting light into said fluid in a predetermined direction; reflecting means for reflective said light in said predetermined direction; and, further light conducting means for conducting said reflected light to said measuring means.

13. The arrangement of claim 12, said first-mentioned light conducting means and said further light conducting means consisting of light conductors.

14. The arrangement of claim 12, said illuminating means comprising an illuminating device for generating said white light; said first-mentioned light conducting means and said further light conducting means being a branched light conductor having a first branch communicating with said illuminating device and a second branch communicating with said measuring means, said branched light conductor having a common branch end mounted in front of said second light transmitting window.

15. The arrangement of claim 10, wherein the fluid is intensely absorbent in a predetermined wavelength range, the arrangement further comprising filter means disposed between said illuminating device and said second light transmitting window, said filter means being dimensioned so as to have a low transmittance in said predetermined wavelength range so that said measuring means delivers no measured value output in said predetermined wavelength range.

16. The arrangement of claim 14, wherein the fluid is partially absorbent in a predetermined wavelength range, and the arrangement further comprising a double monochromator having oppositely directed dispersion, said double monochromator being disposed between said illuminating device and said second light transmitting window and including adjustable central slit means for passing only said predetermined wavelength range so that said measuring means delivers a measured value output in said predetermined wavelength range.

17. The arrangement of claim 16, said double monochromator including electric control means for adjusting said central slit means, said electric control means being connected to said computer.

* * * * *

UNITED STATES PATENT AND TRADEMARK OFFICE
CERTIFICATE OF CORRECTION

PATENT NO. : 4,660,974

DATED : April 28, 1987

INVENTOR(S) : Meinrad Mächler et al

It is certified that error appears in the above-identified patent and that said Letters Patent is hereby corrected as shown below:

In column 6, line 55: delete "31b" and substitute -- 31b' -- therefor.

In column 7, line 65: "$dn/n \cong d\lambda/\lambda_1 - \lambda_j$" and substitute -- $dn/n \cong d\lambda/\lambda_i - \lambda_j$ -- therefor.

In column 8, line 44: delete "componsent" and substitute -- component -- therefor.

In column 10, line 10: delete "reflective" and substitute -- reflecting -- therefor.

Signed and Sealed this

Tenth Day of November, 1987

Attest:

DONALD J. QUIGG

*Attesting Officer*     *Commissioner of Patents and Trademarks*